(12) United States Patent
Brehm et al.

(10) Patent No.: US 6,911,499 B1
(45) Date of Patent: Jun. 28, 2005

(54) POLYMER COMPOSITION AND A METHOD FOR PRODUCING THE SAME

(75) Inventors: Helmut Brehm, Krefeld (DE); Hans-Georg Hartan, Kevelaer (DE)

(73) Assignee: Stockhausen GmbH, Krefeld (DE)

( * ) Notice: Subject to any disclaimer, the term of this patent is extended or adjusted under 35 U.S.C. 154(b) by 0 days.

(21) Appl. No.: 10/069,278

(22) PCT Filed: Aug. 2, 2000

(86) PCT No.: PCT/EP00/07479

§ 371 (c)(1),
(2), (4) Date: Jun. 11, 2002

(87) PCT Pub. No.: WO01/16197

PCT Pub. Date: Mar. 8, 2001

(30) Foreign Application Priority Data

Aug. 30, 1999 (DE) .......................................... 199 41 423

(51) Int. Cl.⁷ .............................. C08F 20/02; C08J 9/28
(52) U.S. Cl. ................................. 525/329.7; 525/330.2; 525/358; 525/244; 525/262; 523/105; 523/111; 523/173; 526/201; 526/213
(58) Field of Search .......................... 525/329.7, 330.2, 525/358, 244, 262; 523/105, 111, 173, 339; 526/201, 213

(56) References Cited

U.S. PATENT DOCUMENTS

| | | | |
|---|---|---|---|
| 4,690,788 A | * | 9/1987 | Yada et al. ................... 264/22 |
| 5,145,906 A | | 9/1992 | Chambers et al. |
| 5,409,771 A | | 4/1995 | Dahmen et al. |
| 5,453,323 A | | 9/1995 | Chambers et al. |
| 5,712,316 A | | 1/1998 | Dahmen et al. |
| 5,837,789 A | | 11/1998 | Stockhausen et al. |

FOREIGN PATENT DOCUMENTS

| | | |
|---|---|---|
| DE | 42 44 548 A1 | 12/1992 |
| DE | 44 18 818 A1 | 5/1994 |
| DE | 195 29 348 A1 | 8/1995 |
| DE | 196 25 143 C1 | 8/1997 |
| DE | 198 46 412 A1 | 4/2000 |
| DE | 198 46 413 A1 | 4/2000 |
| WO | WO 97/18889 | 5/1997 |

OTHER PUBLICATIONS

Omidian, H., et al., Modifying Acrylic–Based Superabsorbents. I. Modification of Crosslinker and Comonomer Nature, Journal of Applied Polymer Science, (1994), page(s) 241–249 vol. 54.

Guojie Wang, et al., Inverse Suspension Polymerization of Sodium Acrylate, Journal of Applied Polymer Science, (1997), pp. 789–794, vol. 65.

* cited by examiner

Primary Examiner—James J. Seidleck
Assistant Examiner—Olga Asinovsky
(74) Attorney, Agent, or Firm—Smith Moore LLP

(57) ABSTRACT

The present invention relates to powdered, crosslinked polymer compositions, containing
a) 55–99.9 wt.-% of at least one polymerized, ethylenically unsaturated, polymerizable monomer which contains acid groups neutralized to at least 25 mole-%,
b) 0–40 wt.-% of polymerized, unsaturated monomers copolymerizable with a),
c) 0.01–5.0 wt.-%, preferably 0.1–2.0 wt.-% of one or more crosslinking agents,
d) 0–30 wt.-% of a water-soluble polymer,
the weight amounts a) through d) being based on anhydrous polymer composition, and the sum of these components always being 100 wt.-%, which compositions can be obtained by continuous polymerization wherein at least one parameter biasing the polymerization is varied according to a recurring pattern. The present invention also relates to a process for their production and to their use.

7 Claims, No Drawings

POLYMER COMPOSITION AND A METHOD FOR PRODUCING THE SAME

This application is a national stage application under 35 U.S.C. 371 of International Application No. PCT/EP2000/07479 filed Aug. 2, 2000, which is based on German Application No. DE 199 41 423.8 filed on Aug. 30, 1999, and claims priority thereto.

The invention relates to a continuous process for producing hydrophilic, swellable polymer compositions for aqueous liquids.

Polymer products absorbing large amounts of aqueous liquids, particularly body fluids such as urine, are known as superabsorbent polymers.

These polymers are produced by free-radical polymerization, preferably using monoethylenically unsaturated carboxylic acids such as acrylic acid and the alkali salts thereof in aqueous solution, or according to the processes of inverse suspension or emulsion polymerization, such as described in U.S. Pat. No. 4,286,082, DE 27 06 135, U.S. Pat. No. 4,340,706, DE 37 13 601, and DE 28 40 010.

By selecting the monomer composition, the crosslinkers, as well as polymerization conditions and processing conditions for the polymer gel, polymer products having distinct absorber properties can be produced. Further options of variation are provided by the production of graft polymers, e.g. using chemically modified starch, cellulose and polyvinyl alcohol according to DE-OS 25 12 846, and the secondary treatment of polymer gels or powdered resins by secondary crosslinking of the surface of polymer particles, e.g. according to DE 40 20 780 C1.

In order to use these polymers in the hygiene and sanitary sectors, polymers are produced wherein the degree of neutralization approximately is between 50 and 80 mole-%, relative to the polymerized monomer units containing acid groups, so that hydrogels are formed which have a skin-neutral effect when used.

During the further technical development of superabsorbing polymers, the pattern of requirements to be met by these products has been changing significantly over the years. While initially, the exceedingly high swelling power upon contact with a liquid was the only point which had been given special emphasis during the development of superabsorbers, it has later been found that not only the amount of liquid absorbed, but also the strength of the swollen gel is important. However, as is already known from U.S. Pat. No. 3,247,171, the retention on the one hand, and the strength of the swollen gel on the other hand, are contrary properties. Consequently, polymers having a particularly high retention have only low strength of the swollen gel and as a result, the gel is deformable under an applied pressure (e.g., the pressure of the body), preventing further absorption of liquid. This specific property of absorption, referred to as "absorption under pressure" (AUP), has been described in U.S. Pat. No. 5,314,420, for example.

As a result of the increased demands to be met by superabsorbers in the hygiene sector, the original load of 21 g/cm$^2$ (0.3 psi) was found to be no longer the desired standard of properties required for incontinence products or diaper constructions with low fluff content and high amounts of superabsorber. Consequently, pressure loads of 49 g/cm$^2$ (0.7 psi) are demanded today.

While a person skilled in the art will know about methods of producing e.g. products having high retention or high absorption or low solubles or rapid absorption of water, simultaneous adjustment of all these four positive properties has not been possible with previously known formulations.

Thus, it is well-known to a person skilled in the art that increasing the crosslinker concentration will result in products low in solubles, but at the same time, products having low retention are obtained. Conversely, while decreasing the crosslinker concentration will afford products having high retention, the solubles will be high as well.

The development towards thinner and thinner diaper constructions in the hygiene sector is associated with a higher compacting of the absorbent core and an increase of the superabsorber ratio in the superabsorber/cellulose mixture. As a result, the homogeneous liquid distribution within the absorbent core becomes a more and more important criterion for full-scale utilization of the storage capacity of highly swellable polymers.

The reduction of the cellulose amount in the absorbent core has an adverse effect on the liquid distribution. Meanwhile, the use of additional means such as special fleeces in order to optimize the liquid distribution has become state of the art.

Additional demands with respect to the liquid management are made on the highly swellable, liquid-storing polymers as well. Even in a superabsorber/cellulose mixture having a high ratio of highly swellable polymers, the liquid-storing polymers must permit or support rapid distribution of liquid within the superabsorber/cellulose mixture.

Conventional superabsorbers which are frequently optimized for a high liquid absorption rate in particular, have a tendency to absorb and store an aqueous liquid immediately upon contact with such a liquid, which is associated with a massive volume increase of the polymer particles.

In the vicinity of the entry site of body fluid into the absorbent core, the absorbent polymers undergo massive swelling as a result of their high absorption rate for aqueous liquids, because the distribution of liquid is slower than the liquid storage by the highly swellable polymer as a result of the low cellulose ratio in the absorbent core. Owing to this rate difference, a major part of the liquid is absorbed in the immediate vicinity of the entry site.

Moreover, this effect is reinforced in that the swelling of a conventional superabsorber takes place in such a way that immediately upon addition of liquid, a very high absorption rate for aqueous liquids is observed, in association with a steep increase of absorption. After a few minutes already, a highly swellable polymer based on crosslinked, partially neutralized polyacrylate has reached about 95% of its absorptive capacity under conditions of free swelling. Thereafter, the amount of absorbed liquid asymptotically approaches its equilibrium value. As a result, an excessive proportion of liquid per unit time is taken up by the described highly swellable polymers immediately after addition of the liquid to be absorbed. This behavior is a typical material property of crosslinked polyacrylates.

As a result of the expansion of the polymer particles associated with the absorption of liquid, the interstices and pores of the SAP/fluff matrix close within the absorbent core area around the entry site of the body fluid. As the liquid transport through a swelled hydrogel by diffusion is some magnitudes slower compared to the flow in interstices, blocking occurs in this area. Succeeding amounts of body fluid cannot penetrate the absorbent core and will be transported randomly over the surface of the already surface-saturated area up to the edge of same.

As a consequence, the reverse wetting behavior and leakage behavior of the hygiene article are deteriorated. In addition, the storage capacity of the absorbent core is reduced because highly absorbent polymers embedded deeper in the absorbent core can no longer be reached by additional body fluid from later dosages as a result of swelling of the particles at the surface and thus, cannot contribute to the overall storage capacity.

To correct these drawbacks of absorbent bodies, U.S. Pat. No. 5,728,082 suggests the use of two different superabsorbers separated from each other in the absorbent core.

A highly crosslinked polymer, i.e., a highly permeable superabsorber having low retention, is placed in an upper layer, and a polymer having higher retention, i.e., lower crosslinking, is placed in a second layer.

EP 0,640,330 A1 claims an absorbent construction which, inter alia, includes two separate layers of swellable polymers. The upper layer contains a polymer having a permeability of at least $4 \times 10^{-7}$ cm$^3$·s/g in the swollen state, while the lower polymer layer exhibits an absorption under a load of 50 g/cm$^2$ of at least 15 g/g and a swelling rate of at least 0.2 g/g·s.

Crosslinked, water-swellable polymer products having improved permeability, retention, and absorption under pressure are known from DE 195 43 366 A1, which are produced using unsaturated aminoalcohols. DE 195 43 368 A1 describes polymer products having improved absorption under pressure, where crosslinker mixtures of diacrylates and alkoxylated allyl ether acrylates are used in the synthesis thereof. Liquid-absorbing polymer products having improved permeability, absorption under pressure, and high absorption rate can be inferred from DE 196 46 484 A1, which are produced using a combination of alkoxylated crosslinker and alkoxylated monomer.

It is the object of the invention to provide polymer compositions and a process for producing same, which compositions exhibit both high absorption for aqueous liquids under a load of 50 g/cm$^2$ and high permeability of the swollen gel for aqueous liquids. In addition, the polymer compositions should have a pattern of properties which at present can only be achieved by using combinations of polymer products to be employed separately.

According to the invention, said object is accomplished by providing a powdered, crosslinked polymer product containing
a) 55–99.9 wt.-% of at least one polymerized, ethylenically unsaturated, polymerizable monomer which contains acid groups neutralized to at least 25 mole-%,
b) 0–40 wt.-% of polymerized, unsaturated monomers copolymerizable with a),
c) 0.01–5.0 wt.-%, preferably 0.1–2.0 wt.-% of one or more crosslinking agents,
d) 0–30 wt.-% of a water-soluble polymer,
the weight amounts a) through d) being based on anhydrous polymer composition, and the sum of these components always being 100 wt.-%, which composition can be obtained by continuous polymerization wherein at least one parameter biasing the polymerization is varied according to a recurring pattern.

According to the invention, water-soluble, monoethylenically unsaturated mono- and dicarboxylic acids preferably are employed as polymerizable, unsaturated monomers a) containing acid groups, with acrylic acid, methacrylic acid, ethacrylic acid, crotonic acid, sorbic acid and maleic acid, fumaric acid, itaconic acid, as well as vinylsulfonic acid, acrylamido- and/or methacrylamidoalkylsulfonic acids such as 2-acrylamido-2-methylpropanesulfonic acid, 2-methacryloyloxyethanesulfonic acid, 4-vinylbenzenesulfonic acid, allylsulfonic acid, vinyltoluic acid, vinylphosphonic acid, and vinylbenzenephosphonic acid being particularly preferred. The acidic monomer components are neutralized to at least 25 mole-%, preferably at least 50 mole-%, and more preferably from 50 to 80 mole-%.

A particularly preferred water-soluble unsaturated carboxylic acid is acrylic acid which preferably is employed as the only acid group-containing monomer in the polymer compositions of the invention and preferably is neutralized to 50–80 mole-%. It is also preferred that the percentage of other unsaturated carboxylic acids in addition to acrylic acid in the polymer product is up to 50 wt.-%.

Water-soluble, monoethylenically unsaturated monomers preferably are used as monomers b), with acrylamide, methacrylamide, N-alkylated (meth)acrylamides, N-methylol (meth)acrylamide, N-vinylamides, N-vinylformamide, N-vinylacetamide, N-vinyl-N-methylacetamide, N-vinyl-N-methylformamide, vinylpyrrolidone, as well as hydroxyalkyl (meth)acrylates such as hydroxyethyl acrylate, and (meth)acrylic esters of polyethylene glycol monoallyl ether, and allyl ethers of polyethylene glycols being particularly preferred.

As monomers b), it is also preferred to use limited amounts of monomers having low solubility in water, with acrylates and methacrylates such as ethyl acrylate and methyl acrylate, vinyl acetate and styrene being particularly preferred. The percentage of these sparingly or limitedly water-soluble monomers preferably is 10 wt.-% at maximum, relative to the sum of all monomers.

The monomers can be polymerized alone in solution or, in order to obtain co- and terpolymer compositions, as a mixture with other monomers. Those skilled in the art will recognize that more than three monomers can also be polymerized together.

According to the invention, the aqueous monomer solution includes at least one crosslinker c) in an amount of 0.01–5.0 wt.-%, preferably 0.1–2.0 wt.-%, relative to the anhydrous composition of the invention. Preferably, all those compounds including at least two ethylenically unsaturated double bonds or one ethylenically unsaturated double bond and one functional group reactive towards acid groups or multiple functional groups reactive towards acid groups are used as crosslinkers. Examples of these are: methylenebisacrylamide, acrylates and methacrylates of polyols, such as butanediol diacrylate, hexanediol dimethacrylate, polyethylene glycol diacrylate, and trimethylolpropane triacrylate, and/or acrylates and methacrylates of the oxyalkylated above-mentioned polyols, e.g. those of oxyalkylated trimethylolpropane and oxyalkylated pentaerythritol. Crosslinkers of this type are known under the trade names of Sartomer and Craynor (Crayvalley Kunstharze GmbH, DE-47918 Tönisvorst, Germany), among which Sartomer 415, Sartomer 454, Sartomer 494, Sartomer 610, and Craynor 435 can be used in particular, and also, di- and polyesters of polyols and oxyethylated polyols with unsaturated monocarboxylic acids and/or polycarboxylic acids, such as (meth)acrylic esters of 1,2-propylene glycol pentaerythritol, glycerol and polyglycerol, as well as monoesters of unsaturated alcohols and ethoxylated unsaturated alcohols with unsaturated monocarboxylic acids and/or monocarboxylic acids, such as allyl acrylate and methacrylate, monoallyl maleate, allylpolyethylene glycol ether acrylate and methacrylate, allyl itaconate, allylpolyethylene glycol ether itaconate, and monoallylpolyethylene glycol ether maleate, and also, diallylacrylamide, diallyl phthalate, diallyl adipate, triallyl citrate, and trimonoallylpolyethylene glycol ether citrate, as well as allyl ethers of di- and polyols and oxyethylates thereof, such as diallyl ethers of ethylene glycol, diethylene glycol, polyethylene glycol, triallyl ethers of glycerol, oxyethylated glycerol, trimethylolpropane and oxyethylated trimethylolpropane, tetraallyl ethers of pentaerythritol and oxyethylated pentaerythritol, as well as tetraallyloxyethane and polyglycidylethers such as ethylene glycol diglycidyl ether and glycerol glycidyl ether; furthermore, amines and/or salts thereof, amides having at least two ethylenically unsaturated alkyl groups, such as di- and triallylamine and tetraallylammonium chloride.

The monomer mixture may also include water-soluble polymers d) in an amount of 0–30 wt.-%, preferably 1–5 wt.-%, relative to the anhydrous polymer composition according to the invention. Examples of these are water-soluble homo- or copolymers of the above-mentioned monomers, such as polyacrylic acid, partially saponified polyvinyl acetate, polyvinyl alcohol, polyalkylene glycol, starch, starch derivatives, graft-polymerized starch, cellulose and cellulose derivatives such as carboxymethylcellulose, hydroxymethylcellulose, as well as galactomannans and oxyalkylated derivatives thereof. The water-soluble polymer preferably is starch and/or polyvinyl alcohol.

Conventional initiators, e.g. peroxo and azo compounds, preferably peroxo and azo compounds soluble and/or dissociating in water, such as tert-butyl hydroperoxide and 2,2'-azobis(2-methylpropionamidine) dihydrochloride, as well as redox systems formed of sodium and potassium peroxomonosulfate, sodium and potassium peroxodisulfate and hydrogen peroxide with sodium and potassium sulfite, sodium and potassium formamidinesulfinate and ascorbic acid are used to initiate the free-radical polymerization.

When using redox systems, the oxidizing agent preferably is charged first, and the reducing agent is added subsequently. Particularly in continuous polymerization, initiation is effected by photocatalysis using UV light and well-known sensitizers.

According to the invention, at least one parameter biasing the polymerization is varied according to a recurring pattern in this continuous process.

In the meaning of the invention, "according to a recurring pattern" means that the parameters biasing the polymerization are varied in any desired manner, but at regularly recurring time intervals within a reasonable spectrum, and preferably in a continuous fashion.

The pattern preferably is an oscillation about a random mean value. Said oscillation preferably is harmonic or anharmonic and preferably undamped.

The parameters preferably are varied prior to starting the polymerization, e.g., in the supply of the preferably aqueous monomer solution onto the moving support, the following parameters preferably being subject to variation:
a) the composition of the monomer solution in the production of co- and terpolymers, by varying the amount of at least one monoethylenically unsaturated monomer according to a recurring pattern,
b-1) the percentage of one or more compounds containing at least two ethylenically unsaturated double bonds, by varying their metered amount according to a recurring pattern,
b-2) the percentage of one or more compounds containing one ethylenically unsaturated double bond and one or more functional groups reactive towards acid groups, by varying their metered amount according to a recurring pattern,
b-3) the percentage of one or more compounds containing multiple functional groups reactive towards acid groups, by varying their metered amount according to a recurring pattern,
c) the amount of catalyst, by increasing and reducing the concentration of catalyst or catalyst system according to a recurring pattern,
d) the amount of molecular weight modifier, by increasing and reducing the amount of molecular weight modifier solution according to a recurring pattern,
e) the pH value or degree of neutralization of the monomer solution, by increasing and reducing the alkali, alkaline earth or ammonia metering according to a recurring pattern,
f) the graft basis, by increasing and reducing the amount of graft basis according to a recurring pattern.

Among these parameters, one or more can be varied simultaneously or at different times.

Preferably, the pattern is an oscillation about a mean value that can be selected at random. Amplitude and frequency of the oscillation can be selected at random. While the frequency, i.e., the time during which the pattern of varying a polymerization parameter is carried out once, is determined by the sizing of the plant components, the amplitude, i.e., the level of the continuously performed variation, is crucial for the application-technical properties of the polymer compositions.

Those skilled in the art will recognize that varying one parameter may result in the variation of other polymerization parameters. When varying the amount of catalyst metering in the reactor feed, for example, the concentration of free radicals in the monomer solution and thus, the polymerization rate on the polymerization belt will be subject to continuous change which can be recognized in an oscillating temperature profile.

The polymer gel having formed is crushed according to well-known methods and dried to a water content of about 10% at temperatures ranging from 100 to 190° C.

Subsequently, the dried material is milled to a polymer powder having a grain size ranging from 20 to 3000 µm, preferably from 150 to 850 µm, and screened.

Following milling and screening, the polymer powder preferably is subjected to secondary crosslinking. Secondary crosslinking of the polymer product is effected on the surface of the dried polymer particles using at least one bi- or polyfunctional crosslinking agent reacting with acid groups, preferably carboxyl groups, which agent preferably is applied in the form of an aqueous solution. Polyols such as ethylene glycol, 1,2-propylene glycol, 1,4-butanediol, glycerol, di- and polyglycerol, pentaerythritol, oxyethylates of these polyols, as well as their esters with carboxylic acids or carbonic acid are suitable as secondary crosslinking agents. Addition of an esterification catalyst, e.g. p-toluenesulfonic acid or phosphorus acid is advantageous. Other suitable crosslinking agents are di- and polyglycidyl ethers of polyols and polyethylene glycols. Such compounds are commercially available under the trade name of Denacol® (Nagase (Europe) GmbH, Duesseldorf, Germany). The secondary crosslinkers preferably are employed in amounts of from 0.05 to 3 wt.-%, relative to the polymer composition.

Secondary crosslinking preferably is performed at temperatures ranging from 150 to 250° C., more preferably from 150 to 200° C. in a mixing apparatus, preferably in a Nara mixer.

The polymer composition of the invention can be used with particular advantage as an absorbent for water and aqueous liquids, as an absorbent in constructions used to absorb body fluids, as an absorbing component in electroconductive or light-conducting cables and packaging materials, as soil improver, in plant breeding, as an absorbent for water and aqueous liquids in preferably foamed sheet materials, and as vehicle for fertilizers or other active ingredients released over a prolonged period of time. Therefore, the present invention is also directed to these uses.

The present invention is also directed to a continuous process for producing the powdered, crosslinked polymer compositions of the invention which absorb aqueous or serous fluids, as well as blood, and include:
a) 55–99.9 wt.-% of at least one polymerized, ethylenically unsaturated, polymerizable monomer which contains acid groups neutralized to at least 25 mole-%,
b) 0–40 wt.-% of polymerized, unsaturated monomers copolymerizable with a),
c) 0.01–5.0 wt.-%, preferably 0.1–2.0 wt.-% of one or more crosslinking agents,
d) 0–30 wt.-% of a water-soluble polymer,
the weight amounts a) through d) being based on anhydrous polymer composition, and the sum of these components always being 100 wt.-%. In the process according to the invention, at least one parameter biasing the polymerization is varied according to a recurring pattern.

As to the components a) through d), reference is made to the disclosure relating to the polymer composition of the invention.

The polymerization is performed according to any process well-known to those skilled in the art. The polymerization preferably is a solution polymerization. The continuous solution polymerization preferably is carried out on a moving support as taught e.g. in EP 0,296,331 B1 or EP 0,228,638 B1 which hereby are incorporated by reference and thus represent part of the disclosure. In these patent specifications, the moving support is a conveying belt onto which an aqueous monomer solution made free of oxygen is metered, which solution undergoes polymerization upon addition of catalyst to form a solid gel, liberating the heat of polymerization.

In the continuous process according to the invention, at least one parameter biasing the polymerization is varied according to a recurring pattern.

In the meaning of the invention, "according to a recurring pattern" means that the parameters biasing the polymerization are varied in any desired manner, but at regularly recurring time intervals within a reasonable spectrum, and preferably in a continuous fashion.

The pattern preferably is an oscillation about a random mean value. Said oscillation preferably is harmonic or anharmonic and preferably undamped.

The parameters preferably are varied prior to starting the polymerization, e.g., in the supply of the preferably aqueous monomer solution onto the moving support, the following parameters preferably being subject to variation:
a) the composition of the monomer solution in the production of co- and terpolymers, by varying the amount of at least one monoethylenically unsaturated monomer according to a recurring pattern,
b-1) the percentage of one or more compounds containing at least two ethylenically unsaturated double bonds, by varying their metered amount according to a recurring pattern,
b-2) the percentage of one or more compounds containing one ethylenically unsaturated double bond and one or more functional groups reactive towards acid groups, by varying their metered amount according to a recurring pattern,
b-3) the percentage of one or more compounds containing multiple functional groups reactive towards acid groups, by varying their metered amount according to a recurring pattern,
c) the amount of catalyst, by increasing and reducing the concentration of catalyst or catalyst system according to a recurring pattern,
d) the amount of molecular weight modifier, by increasing and reducing the amount of molecular weight modifier solution according to a recurring pattern,
e) the pH value or degree of neutralization of the monomer solution, by increasing and reducing the alkali, alkaline earth or ammonia metering according to a recurring pattern,
f) the graft basis, by increasing and reducing the amount of graft basis according to a recurring pattern.

Among these parameters, one or more can be varied simultaneously or at different times.

Preferably, the pattern is an oscillation about a mean value that can be selected at random. Amplitude and frequency of the oscillation can be selected at random. While the frequency, i.e., the time during which the pattern of varying a polymerization parameter is carried out once, is determined by the sizing of the plant components, the amplitude, i.e., the level of the continuously performed variation, is crucial for the application-technical properties of the polymer compositions.

Those skilled in the art will recognize that varying one parameter may result in the variation of other polymerization parameters. When varying the amount of catalyst metering in the reactor feed, for example, the concentration of free radicals in the monomer solution and thus, the polymerization rate on the polymerization belt will be subject to continuous change which can be recognized in an oscillating temperature profile.

The polymer gel having formed is crushed according to well-known methods and dried to a water content of about 10% at temperatures ranging from 100 to 190° C.

Subsequently, the dried material is milled to a polymer powder having a grain size ranging from 20 to 3000 μm, preferably from 150 to 850 μm, and screened.

Following milling and screening, the polymer powder preferably is subjected to secondary crosslinking. Secondary crosslinking of the polymer product is effected on the surface of the dried polymer particles using at least one bi- or polyfunctional crosslinking agent reacting with acid groups, preferably carboxyl groups, which agent preferably is applied in the form of an aqueous solution. Polyols such as ethylene glycol, 1,2-propylene glycol, 1,4-butanediol, glycerol, di- and polyglycerol, pentaerythritol, oxyethylates of these polyols, as well as their esters with carboxylic acids or carbonic acid are suitable as secondary crosslinking agents. Addition of an esterification catalyst, e.g. p-toluenesulfonic acid or phosphorus acid is advantageous. Other suitable crosslinking agents are di- and polyglycidyl ethers of polyols and polyethylene glycols. Such compounds are commercially available under the trade name of Denacol® (Nagase (Europe) GmbH, Duesseldorf, Germany). The secondary crosslinkers preferably are employed in amounts of from 0.05 to 3 wt.-%, relative to the polymer composition.

Secondary crosslinking preferably is performed at temperatures ranging from 150 to 250° C., more preferably from 150 to 200° C. in a mixing apparatus, preferably in a Nara mixer.

To carry out the process according to the invention, e.g. the continuous polymerization described in EP 0,296,331 B1, Example 4 and FIG. 2 is modified in such a way that the mass flow of catalyst solutions is varied by means of metering valves 28 and 30 according to a preselected pattern along a controlled system at regular time intervals in a recurring fashion. The above-mentioned patent specification hereby is incorporated by reference and thus represents part of the disclosure.

In a preferred embodiment of the process according to the invention, a constant amount of a catalyst system is metered into the constant flow of a partially neutralized solution of acrylic acid purged with nitrogen and present with 70 mole-% as sodium acrylate. A solution of triallylamine crosslinker in methacrylic acid is metered from another reservoir in an amount continuously varying in the form of a sine-shaped oscillation. Depending on the concentration and amount of crosslinker solution, not only the crosslinking density and neutralization level but also the monomer concentration on the polymerization belt undergo a periodic change, giving rise to a continuously changing temperature profile in the polymer gel as a result of the exothermic reaction. As plug flow in the line is largely retained at the end of the dryer, samples taken at intervals of 5 minutes clearly show varying crosslinking density which can be recognized in the varying absorption capacity for physiological saline.

In another preferred embodiment of the process according to the invention, following continuous addition of the catalysts, a periodically varying amount of an aqueous solution of e.g. PEG(polyethylene glycol) 400 diacrylate is additionally metered into the constant feed flow of an acrylic acid solution purged with nitrogen and neutralized to 60 mole-% with sodium hydroxide solution, which already includes a crosslinker, e.g. allylpolyethylene glycol ether acrylate. The samples taken at the end of the dryer exhibit liquid absorption which varies in the form of an oscillation. Once the dried polymer has passed those parts of the line having massive back mixing, such as milling cycle, screening and silo mixer, a bulk material is obtained which is virtually homogeneous when tested.

In another preferred embodiment of the process according to the invention, following continuous addition of the catalysts, a periodically varying amount of an aqueous solution of a non-ionogenic monomer, e.g. methoxy-PEG (polyethylene glycol) 750 methacrylate is additionally metered into the constant feed flow of an acrylic acid solution purged with nitrogen and neutralized to 70 mole-% with sodium hydroxide solution, which already includes a crosslinker, e.g. allylpolyethylene glycol ether acrylate.

Instead of such a non-ionogenic monomer, it is also possible to meter a solution of a graft basis such as polyvinyl alcohol and vary the amount thereof according to a recurring pattern.

If the solution of the graft basis contains a modifier such as formic acid, acetic acid or isopropanol, its amount relative to the monomer will also vary periodically. It is highest, however, when the graft basis reaches its highest concentration in the polymerizing solution.

It is well-know to those skilled in the art that polymer gels having different crosslinking densities, different degrees of neutralization, different temperatures etc. may markedly differ after polymerization with respect to their ability of being cut, dried and milled.

It is therefore suggested to perform the polymerization on two polymerization belts operated in parallel. If the parameters biasing the polymerization are varied in a phase-shifted fashion—e.g., when the crosslinker concentration on the one belt is about to reach a maximum, the concentration on the other belt is about to reach a minimum—the gel strands can be crushed, dried and milled together under constant conditions.

The polymer compositions of the invention involve the advantage of straightforward production on existing plants and of covering a wide spectrum of superabsorbing polymers.

In particular, this is the case with polymer compositions having undergone a secondary surface crosslinking.

As a result of secondary crosslinking in the surface layer of the polymer particles, a polymer composition is formed covering a wide spectrum of secondary-crosslinked superabsorbing polymers.

For example, a polymer composition according to the invention may have varying ratios of high retention and low crosslinking, in addition to varying ratios of low retention and high absorption under load and high gel permeability. In use, the properties of these polymer compositions are superior to those of mixtures described in the prior art.

The invention will be illustrated with reference to the Examples hereinbelow which, however, are not intended to limit the general idea of the invention.

Test Methods

Tea Bag Retention (TB)

This test is performed according to the statements in EP 0,640,330 A1 under "Tea Bag Retention Capacity Test".

Absorption Under Load (AUL)

This test is performed according to the statements in EP 0,640,330 A1 under "Absorption Against Pressure Test" at loads of 20 g/cm$^2$ (0.3 psi) and 50 g/cm$^2$ (0.7 psi).

Gel Permeability (GP)

This test is performed according to the statements in EP 0,640,330 A1 under "Gel Layer Permeability Test".

Passing Rate (PR)

The test is performed according to the statements in EP 594,009 B1 under "Method for measuring passing rate of physiological saline".

EXAMPLES

Abbreviations:

Methoxypolyethylene glycol(17EO) methacrylate=MPEG-MAC

Polyethylene glycol(10EO) allyl ether acrylate=PEGMAE-AC

Sodium peroxodisulfate=NAPS 2,2'-Azobis(2-methylpropionamidine) dihydrochloride= AB-AH Example 1

| Batch: | |
|---|---|
| 4000 | kg of water |
| 2030 | kg of sodium hydroxide solution, 50% |
| 2610 | kg of acrylic acid |
| 23.5 | kg of PEGMAE-AC |
| 8663.5 | kg of monomer solution |

400 kg/h of this monomer solution is cooled to 1° C. in a heat exchanger and made free of dissolved oxygen to a residual content of 0.9 ppm in a stripper swept with 3 m$^3$/h of nitrogen. Prior to placing on the polymerization belt, the following amounts of solutions are mixed with the above feed 1:

Feed 2: 8.8 l/h NAPS solution, 0.75%

Feed 3: 8.8 l/h ABAH solution, 0.5%

Feed 4: 8.8 l/h hydrogen peroxide solution, 0.5%

Feed 5: 8.8 l/h ascorbic acid solution, 0.075%

Feed 6: A solution of 15.66 kg of polyethylene glycol 300 diacrylate and 162 kg of water, the metering rate of which is varied with a steady increase from 5 kg/h to 10 kg/h and with a steady decrease to 5 kg/h over a time period of 30 minutes. This pattern of varying amounts is maintained throughout the entire test period.

Following a residence time of 40 minutes, the solid polymer gel, still being hot, is reduced in size in a meat grinder and dried on a belt dryer at an inlet air temperature of 160° C. in zones 1 and 2, 140° C. in zone 3, and 130° C. in zones 4 and 5. Samples taken at the end of the dryer at intervals of 5 minutes exhibit the following retentions:

| Time [min] | | | | | | | |
|---|---|---|---|---|---|---|---|
| | 0 | 5 | 10 | 15 | 20 | 25 | 30 |
| TB [g/g] | 27 | 27.5 | 28 | 29 | 28.5 | 27 | 26.5 |

The milled silo sample screened to 150–850 μm has the following grain size distribution:

| Screen analysis | | | | | |
|---|---|---|---|---|---|
| Mesh width [μm] | 850 | 600 | 300 | 150 | 45 |
| % on screen | 0.1 | 3.9 | 67.3 | 28.6 | 0.1 |

Examples 1a and 1b

The polymer composition of Example 1 is conveyed continuously into the powder reservoir of a belt weigher using a pneumatic conveyor, and mixed continuously with 2% of a 33.5% ethylene carbonate solution in water through a two-fluid nozzle at a flow rate of 80 kg/h in a vertical tube mixer. Within about 20 minutes, the mixture flows through a steam-heated blade dryer. Following cooling of the polymer powder on a vibratory cooler and pneumatic conveying, protective screening at 1,000 μm and further conveying to the silo are performed. The silo samples exhibit the following characteristics:

| | | | AUL | | |
|---|---|---|---|---|---|
| Example | Steam temp. [°C.] | TB [g/g] | 20 g/cm² [g/g] | 50 g/cm² [g/g] | GP [cm³ · s/g] |
| 1a | 192 | 24.5 | 27 | 24 | 86 × 10⁻⁷ |
| 1b | 190 | 26 | 27.5 | 23.5 | 67 × 10⁻⁷ |

Example 2

| Batch: | |
|---|---|
| 4000 | kg of water |
| 2030 | kg of sodium hydroxide solution, 50% |
| 2610 | kg of acrylic acid |
| 105 | kg of MPEG-MAC |
| 15.7 | kg of PEGMAE-AC |
| 8760.7 | kg of monomer solution |

The above monomer solution, treated as in Example 1, constitutes feed 1 at 400 kg/h, which is mixed upstream the polymerization belt as in Example 1 with the catalyst solutions 2 to 5 specified therein.

Feed 6: A solution of 15 kg of polyethylene glycol 400 dimethacrylate in 200 kg of water, the metering rate of which is varied with a steady increase from 5 kg/h to 15 kg/h and with a steady decrease to 5 kg/h over a time period of 60 minutes. This pattern of varying amounts is maintained throughout the entire test period.

Following a residence time of 40 minutes, the polymer gel is crushed and dried as in Example 1. Samples taken at the end of the dryer at intervals of 5 minutes exhibit the following retentions:

| Time [min] | | | | | | | | | | | | | |
|---|---|---|---|---|---|---|---|---|---|---|---|---|---|
| | 0 | 5 | 10 | 15 | 20 | 25 | 30 | 35 | 40 | 45 | 50 | 55 | 60 |
| TB [g/g] | 35.6 | 36.4 | 37.2 | 36.3 | 35.2 | 34.9 | 34.2 | 33.2 | 33.1 | 31.9 | 32.5 | 33.8 | 35 |

The milled silo sample screened to 150–850 μm has the following grain size distribution:

| Screen analysis | | | | | |
|---|---|---|---|---|---|
| Mesh width [μm] | 850 | 600 | 300 | 150 | 45 |
| % on screen | 0.2 | 25.7 | 60.9 | 13.1 | 0.1 |

Examples 2a and 2b

The polymer composition is subjected to a thermal secondary treatment as in Examples 1a and 1b.

| Secondary treatment and characteristics: | | | | | |
|---|---|---|---|---|---|
| | | | | AUL | |
| Example | EC*/water [%]/[%] | Steam temp. [°C.] | TB [g/g] | 20 g/cm² [g/g] | 50 g/cm² [g/g] | GP [cm³ · s/g] |
| 2a | 0.5/1.0 | 190 | 29.5 | 31 | 26 | 22 × 10⁻⁷ |
| 2b | 1.0/2.5 | 194 | 28 | 28.5 | 23 | 81 × 10⁻⁷ |

*Ethylene carbonate

Comparative Example 1

Examples 2 and 2b are repeated, but using the measure that feed 6 in Example 2 is held constant at 10 kg/h over the time. TB: 34 g/g In the following Table, the characteristics of Example 2b and Comparative Example 1 are supplemented by the passing rate (PR) for physiological saline through the pre-swollen polymer. This test method was performed according to EP 0,594,009 B1.

| | | AUL | | | |
|---|---|---|---|---|---|
| | TB [g/g] | 20 g/cm² [g/g] | 50 g/cm² [g/g] | GP [cm³ · s/g] | PR [ml/min] |
| Example 2b | 28 | 28.5 | 23 | 81 × 10⁻⁷ | 214 |
| Comp. Ex. 1 | 27 | 27.5 | 23.5 | 46 × 10⁻⁷ | 158 |

The polymer product of the invention has a significantly higher permeability.

What is claimed is:

1. A process for the continuous production of powdered, crosslinked polymer compositions absorbing aqueous or serous fluids, as well as blood, comprising:
   a) 55–99.9 wt.-% of at least one polymerized, ethylenically unsaturated, polymerizable monomer which contains acid groups neutralized to at least 25 mole-%;
   b) 0–40 wt. % of polymerized, unsaturated monomers copolymerizable with a);
   c) 0.01–5.0 wt.-% of one or more crosslinking agents;
   d) 0–30 wt.-% of a water soluble polymer, the weight amounts a) through d) being based on anhydrous polymer composition, and the sum of these components always being 100 wt. %, wherein the powdered crosslinked polymer composition is made by continuous polymerization process wherein a parameter of the continuous polymerization process is varied by increasing and decreasing the parameter in a recurring pattern, during the polymerization process.

2. The process according to claim 1, characterized in that said recurring pattern is an oscillation about a mean value which can be selected at random.

3. The process of claim 1, wherein the oscillation is selected from the group consisting of harmonic or anharmonic.

4. The process according to claim 1 characterized in that the polymerization is effected on a moving support.

5. The process according to claim 1 characterized in that the polymer composition is powdered subsequent to dying.

6. The process according to claim 5, characterized in that the powdered polymer product is mixed with 0.05–3 wt.-% of a compound capable of reacting with at least two carboxyl groups and heated to 150–250° C.

7. A process for the continuous production of powdered, crosslinked polymer compositions for absorbing aqueous or serous fluids, as well as blood, comprising:
   a) 55–99.9 wt.-% of at least one polymerized, ethylenically unsaturated, polymerizable monomer which contains acid groups neutralized to at least 25 mole-%;
   b) 0–40 wt.-% of polymerized, unsaturated monomers copolymerizable with a);
   c) 0.01–5.0 wt.-% of a crosslinking agent;
   d) 0–30 wt.-% of a water-soluble polymer, the weight amounts a) through d) being based on anhydrous polymer composition, and the sum of these components always being 100 wt. %, the monomer solution being polymerized to form a gel, said gel being dried and crushed, characterized in that at least one parameter of the continuous polymerization process is varied by increasing and decreasing the parameter in a recurring pattern, during the polymerization process, the parameter selected from the group consisting of the composition of the polymerized, ethylenically unsaturated, polymerizable monomer solution by varying the amount of at least one ethylenically unsaturated monomer, the concentration of the crosslinking agent, the pH value of the monomer solution; and the graft basis by increasing and reducing the amount of graft basis.

* * * * *

UNITED STATES PATENT AND TRADEMARK OFFICE
CERTIFICATE OF CORRECTION

PATENT NO. : 6,911,499 B1
DATED : June 28, 2005
INVENTOR(S) : Helmut Brehm and Hans-Georg Hartan It is certified that error appears in the above-identified patent and that said Letters Patent is hereby corrected as shown below:

Column 3,
Line 12, "inter alia" should be italicized.

Column 9,
Line 46, "well-know" should read -- well-known --.

Column 12,
Third table, at approximately line 42, numbers 20 and 50 are not in proper alignment and should appear in the table as follows:

Secondary treatment and characteristics:

| Example | EC*/water [%][%] | Steam temp. [°C] | TB [g/g] | AUL 20 g/cm² [g/g] | AUL 50 g/cm² [g/g] | GP [cm³·s/g] |
|---------|------------------|------------------|----------|--------------------|--------------------|--------------|
| 2a | 0.5/1.0 | 190 | 29.5 | 31 | 26 | $22 \times 10^{-7}$ |
| 2b | 1.0/2.5 | 194 | 28 | 28.5 | 23 | $81 \times 10^{-7}$ |

*Ethylene carbonate

Signed and Sealed this

Eighth Day of November, 2005

JON W. DUDAS
*Director of the United States Patent and Trademark Office*